(12) United States Patent
Tuke et al.

(10) Patent No.: US 11,969,358 B2
(45) Date of Patent: Apr. 30, 2024

(54) PROSTHESIS IMPACTOR ASSEMBLY

(71) Applicant: MATORTHO LIMITED, Leatherhead (GB)

(72) Inventors: Michael Antony Tuke, Leatherhead (GB); Charles Jonas Ambrose Cullum, Leatherhead (GB); Simon Nicholas Collins, Leatherhead (GB)

(73) Assignee: MATORTHO LIMITED, Leatherhead (GB)

( * ) Notice: Subject to any disclaimer, the term of this patent is extended or adjusted under 35 U.S.C. 154(b) by 725 days.

(21) Appl. No.: 17/257,954

(22) PCT Filed: Jul. 10, 2019

(86) PCT No.: PCT/GB2019/051929
§ 371 (c)(1),
(2) Date: Jan. 5, 2021

(87) PCT Pub. No.: WO2020/012173
PCT Pub. Date: Jan. 16, 2020

(65) Prior Publication Data
US 2021/0145606 A1 May 20, 2021

(30) Foreign Application Priority Data
Jul. 12, 2018 (GB) .................................... 1811421

(51) Int. Cl.
*A61F 2/46* (2006.01)
*A61F 2/30* (2006.01)

(52) U.S. Cl.
CPC .. *A61F 2/4609* (2013.01); *A61F 2002/30565* (2013.01); *A61F 2002/4627* (2013.01); *A61F 2002/4681* (2013.01)

(58) Field of Classification Search
CPC ..................................................... A61F 2/4609
See application file for complete search history.

(56) References Cited

U.S. PATENT DOCUMENTS 5,169,399 A 12/1992 Ryland et al.
2004/0153063 A1 8/2004 Harris, Jr.
(Continued)

FOREIGN PATENT DOCUMENTS

DE 20220090 U1 4/2003
FR 2917288 A1 12/2008
(Continued)

OTHER PUBLICATIONS

International Search Report in corresponding International Patent Application No. PCT/GB2019/051929 mailed Nov. 7, 2019, 6 pages.
(Continued)

*Primary Examiner* — Ariana Zimbouski
*Assistant Examiner* — Jacob Lee Fincher
(74) *Attorney, Agent, or Firm* — Leason Ellis LLP

(57) ABSTRACT

An impactor head (10) for releasably holding an outer surface (12) of a cup implant (14), comprises a head body (16), at least one rotatable implant-engagement arm (20) which is also at least in part linearly translatable, and an actuation mechanism (18) which moves the implant-engagement arm (20) to an implant-engagement condition and an implant-release condition.

12 Claims, 6 Drawing Sheets

(56) References Cited

U.S. PATENT DOCUMENTS

| | | | |
|---|---|---|---|
| 2006/0241781 A1* | 10/2006 | Brown | A61F 2/34 623/22.32 |
| 2007/0219562 A1 | 9/2007 | Slone et al. | |
| 2016/0228262 A1 | 8/2016 | Bailey | |
| 2016/0331551 A1* | 11/2016 | Slade | A61F 2/4609 |

FOREIGN PATENT DOCUMENTS

| | | |
|---|---|---|
| GB | 2299758 A | 10/1996 |
| GB | 2522045 A | 7/2015 |
| WO | 9511641 A1 | 5/1995 |
| WO | 2008099242 A1 | 8/2008 |

OTHER PUBLICATIONS

International Preliminary Report on Patentability in Corresponding International Patent Application No. PCT/GB2019/051929 mailed Jan. 12, 2021. 9 pages.
Examination Report for corresponding British Application No. GB1811421.5, dated Mar. 16, 2022.
Examination Report for corresponding British Application No. 19 750 139.8-1122, dated Nov. 14, 2024 (5 pages).

* cited by examiner

PROSTHESIS IMPACTOR ASSEMBLY

CROSS-REFERENCE TO RELATED PATENT APPLICATIONS

This application is a U.S. National Stage Application under 35 U.S.C. § 371 of International Patent Application No. PCT/GB2019/051929, filed Jul. 10, 2019, which claims the benefit of priority of British Patent Application number GB 1811421.5 filed Jul. 12, 2018, both of which are incorporated by reference in their entireties. The International Application was published on Jan. 16, 2020, as International Publication No. WO 2020/012173 A1.

The present invention relates to an impactor head for releasably holding an outer surface of a cup implant, a surgical introducing kit having a surgical introducer and said impactor head in combination, and to a method of reducing acetabulum bone removal to insert a cup implant gripped on its outer surface by the said impactor head.

Prosthetic cup assemblies are well known and commonly used to provide a functional joint where the corresponding bone has become damaged, diseased or degraded. In particular, the acetabulum of a hip is partially replaced with an acetabular cup assembly. During surgery, an acetabular cup is implanted in the patient's hip using a type of impactor tool. Once implanted in the bone, the spherical head of a femoral implant or of the anatomical femur is receivable within the implanted cup, such that the cup and the femoral implant or femur may act like a ball-and-socket joint.

A first example of such an impactor tool is disclosed in WO 95/11641. The impactor tool comprises a cylindrical head, removably added to the distal end of the handle for actioning the acetabulum to be implanted. The head has four quadrants, of which two are rigid, fixed quadrants diametrically opposed to one another, and the other two are mobile quadrants. Each of the mobile quadrants connects to one of the rigid quadrants by an elastically deformable hinge. The two mobile quadrants can be pivoted by screwing the handle. However, the use of these two mobile quadrants means that the impactor head only engages a small area of the inner face of the acetabular cup, thus with only a limited gripping force and concentrating the force applied to a small surface.

A second example is disclosed in U.S. Pat. No. 5,169,399. This acetabular cup impactor assembly described has a handle attached to a head, and the head has a gripping surface to engage the inner surface of a two-part acetabular cup. The head has two gripping elements or jaws which are spaced apart from each other by a compression spring. To insert the head into the prosthetic cup assembly, the surgeon compresses the spring to bring the two jaws towards each other. Upon release of the spring, the jaws grip the inside of the cup. However, the impactor tool is complex to manufacture and operate with the effort of grip depending directly on the force of the compression spring. Furthermore, in gripping the cup by applying forces to the inside surface, there is a risk of damaging the inside surface of the acetabular cup.

As gripping the inside of the acetabular cup risks damaging the articulating surface of the cup, an impactor tool gripping the outside of the acetabular cup is preferable. However, additional bone would generally need to be removed to accommodate gripping elements external to the cup, such as claws or hooks; such is not accepted in hip surgery. Releasing the cup from the gripping claws could further result in bone being damaged or space being required, particularly if the rim of the cup, or part thereof, is recessed into the bone. In such an operation, it is preferable to remove as little extra bone as possible.

The present invention seeks to provide a solution to these problems by providing an impactor head which is adapted to externally hold different kinds or styles of acetabular cups of different dimensions. The impactor head of the invention ensures both an efficient grip of the cup and a good application of the force of impaction, without damaging the inner surface of the cup whilst reducing an amount of bone interference, disturbance or that needs to be removed.

According to a first aspect of the invention, there is provided an impactor head for releasably holding an outer surface of a cup implant, the impactor head comprising a head body; at least one rotatable implant-engagement arm being at least in part translatable; an actuation mechanism which moves the implant-engagement arm to an implant-engagement condition or an implant-release condition; and an implant outer-surface engagement element which is at or adjacent to a lateral arm end of said implant-engagement arm. Beneficially, the said implant-engagement arm may have a lateral hook portion, the implant outer-surface engagement element being on an inner face of the lateral hook portion. In this case, the impactor head is able to grasp an acetabular cup on the outer surface of the cup via the implant outer-surface engagement element on the lateral hook portion, thereby not damaging the internal surface of the cup. The implant-engagement arm being simultaneously rotatable and translated inwards during motion allows the outer-surface engagement to follow the cup outer surface more closely, thus minimising bone disturbance or bone to be removed.

The terms 'proximal', 'distal', 'medial' and 'lateral' are used to clarify the relative position of features in relation to a central axis of the impactor head and/or device in general. Features which are closer to the surgeon or user when gripping the device are considered to be 'proximal'. Features that are remote from the surgeon or user are considered to be 'distal'.

Furthermore, features which are at or adjacent to a central axis of the impactor head or device may be termed 'medial' or 'proximal'. Those features which are remote relative to the central axis or spaced at or towards a radially outer surface or edge may be termed 'lateral' or 'distal'.

Additionally, the said implant-engagement arm may include a lateral pivot axis about which the implant-engagement arm is rotatable to adopt said implant-engagement condition or said implant-release condition. Beneficially, the lateral pivot axis may be translatable to linearly move the implant-engagement arm radially as it rotates. In this case, the implant-engagement arm is able to engage with the outer surface of the cup by rotating about its pivot and the translation of the implant-engagement arm is inwards into the head or outwards of the head in the radial direction. Additionally, the pivot is also movable with the implant-engagement arm, being mobile relative to the head body.

Furthermore, the head body may include a radial guiding channel in which the lateral pivot axis may be slidable, so that the implant-engagement arm may be translatable to linearly move radially as it rotates. In this case, the pivot axis is mobile relative to the channel and the implant-engagement arm is moveable into and out of along a radius of the head body.

Advantageously, the said implant-engagement arm may be translatable rotatable about a virtual pivot point, so that the implant outer-surface engagement element may be able to follow an arcuate path about a rim of the cup implant. Preferably, the head body has a distal head end and the virtual pivot point is spaced from the lateral pivot axis in a direction of the said distal head end during at least part of the translatable rotation of the implant-engagement arm. Furthermore, the virtual pivot point may be dynamically-movable. This arrangement allows the implant outer-surface engagement element to be in close proximity to the cup outer surface and the implant-engagement arm to be retracted into the head body, thereby reducing the amount of unnecessary bone to be disturbed, compressed and/or removed. Furthermore, the said implant-engagement arm may include a medial pivot axis about which the implant-engagement arm may be rotatable to adopt said implant-engagement condition or said implant-release condition. Additionally, the said actuation mechanism may engage said medial pivot axis to operate the said implant-engagement arm. This arrangement provides a mechanism to act upon the implant-engagement arm via the medial pivot.

Advantageously, the medial pivot axis may be translatable to enable linear movement of the implant-engagement arm radially as it rotates. Optionally, the implant-engagement arm may include a further channel in which the medial pivot axis and/or the lateral pivot axis may be slidable, so that the implant-engagement arm may be translatable to linearly move radially as it rotates. Preferably, the actuation mechanism includes an actuator body receivable at least in part in the cup implant, and an axially-translatable actuator for operating the said rotatably translatable implant-engagement arm. The medial pivot being translatable in both an axial and a radial direction provides further degrees of freedom in the motion of the implant-engagement arm. The actuator mechanism allows transmission of a force applied by the surgeon to alter the condition of the implant-engagement arm.

According to a second aspect of the invention, there is provided an impactor head for releasably holding an outer surface of a cup implant, the impactor head comprising a head body; at least one non-rotatable implant-engagement arm which is radially and axially translatable; an actuation mechanism which moves the implant-engagement arm to an implant-engagement condition or an implant-release condition; and an implant outer-surface engagement element which is at or adjacent to a lateral arm end of said implant-engagement arm. Additionally, the said implant-engagement arm may have a lateral hook portion, the implant outer-surface engagement element being on an inner face of the lateral hook portion. In this case, the impactor head is able to hold an acetabular cup on the outer surface of the cup, thereby not damaging the internal surface of the cup. The implant-engagement arm being solely translatable allows the amount of the bone to be removed or damaged to be minimised.

Beneficially, the head body may include a diagonal guiding channel in which an arm body of said implant-engagement arm may be longitudinally linearly slidable by which the implant-engagement arm may be radially movable to adopt said implant-engagement condition and said implant-release condition. In this case, the impactor head is able to grasp a cup via the implant-engagement arm being able to translate into and out of the implant-engagement condition.

Additionally, the actuation mechanism may include an actuator body receivable at least in part in the cup implant, and an axially-translatable actuator for moving the said non-rotatable translatable implant-engagement arm linearly axially and radially. In this case, the actuator mechanism allows transmission of a force applied by the surgeon to alter the condition of the implant-engagement arm.

Additionally, the head body may have a distal head end and the implant outer-surface engagement element may be moveable on a linear implant-engagement path angled towards the said distal head end of the head body when moving towards the implant-engagement condition. In this arrangement, the amount of bone to be removed or damaged is reduced as much as possible. Additionally, it may be easier to remove bone along a straight line than a curve.

According to a third aspect of the invention, there is provided a surgical introducing kit comprising a surgical introducer in combination with the impactor head, the introducer having an elongate impactor shaft having an attachment element to releasably engage the head body of the impactor head, the attachment element having a user-operable actuator to engage and release the impactor head. Optionally, the attachment element of the introducer may include a remotely operable clamp at the end of the impactor shaft for clamping a receiving head portion on the head body. In this arrangement, the surgical introducing kit allows the surgeon to engage with the head body at a distance, and action the implant-engagement arm. Additionally, when engaged, the surgical introducing kit provides a clear indication of the alignment of the head.

According to a fourth aspect of the invention, there is provided a method of reducing acetabulum bone damage during insertion of a cup implant gripped on its outer surface, the method comprising the steps of: a] providing a dynamically-movable virtual pivot point of the rotatably translatable implant-engagement arm of the impactor head; and b] providing a release path on which the implant outer-surface engagement element travels, the release path originating at the implant-engagement condition of the implant outer-surface engagement element, so that the implant outer-surface engagement element has at least a reduced movement outwardly when moving to the implant-release condition, thereby reducing a bone space required to accommodate a lateral arm end of the implant-engagement arm. This method allows an acetabular cup to be implanted using an impactor head having an implant-engagement arm that is both rotatable and translatable. The result is that no or little extra bone is disturbed, damaged and/or removed.

Alternatively, according to a fifth aspect of the invention, there is provided a method of reducing acetabulum bone damage during insertion of a cup implant gripped on its outer surface, the method comprising the steps of providing the implant outer-surface engagement element of the impactor head with a linear implant-engagement path angled towards a distal head end of the head body when moving towards the implant-engagement condition, so that the implant outer-surface engagement element moves axially and radially outwardly to the implant-release condition, thereby reducing a bone space required to accommodate a lateral arm end of the implant-engagement arm. This method allows an acetabular cup to be implanted using an impactor head having an implant-engagement arm that is solely translatable. The result is that no or little extra bone is disturbed, damaged or removed.

Optionally, either method may be performed using the surgical introducing kit. This method allows an acetabular cup to be implanted using an impactor head having an actionable implant-engagement arm and a surgical introducing kit which transmits a force applied by the surgeon to the actionable implant-engagement arm.

The invention will now be more particularly described, with reference to the accompanying drawings, in which.

Figure 1:
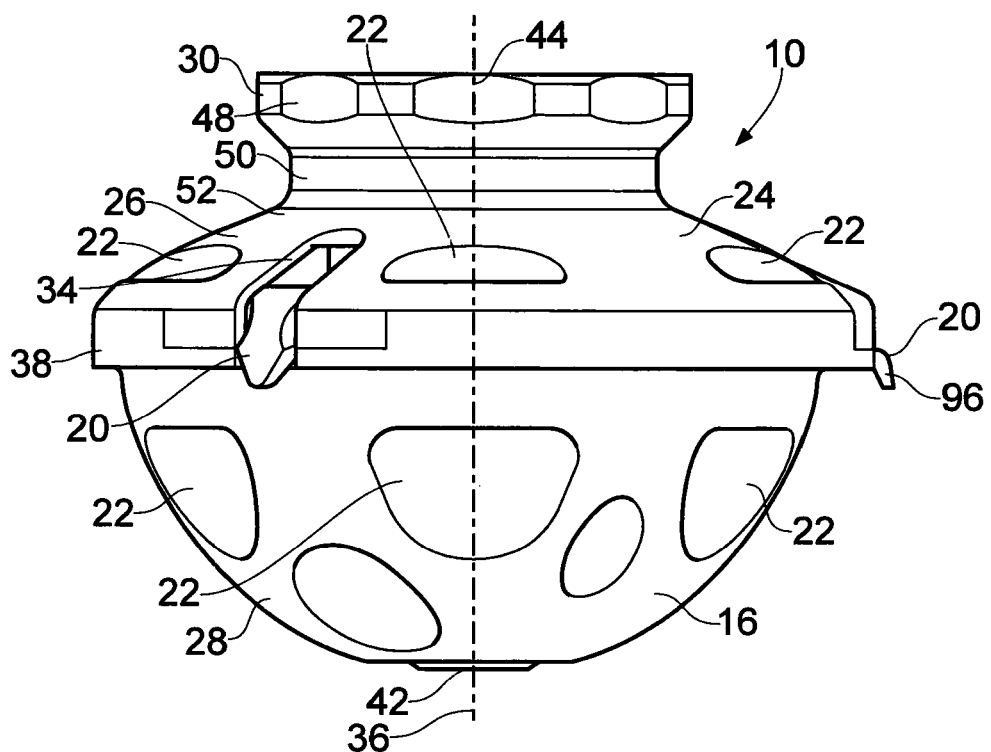
FIG. 1 shows a first embodiment of an impactor head, in accordance with the first aspect of the invention.
Figure 2:
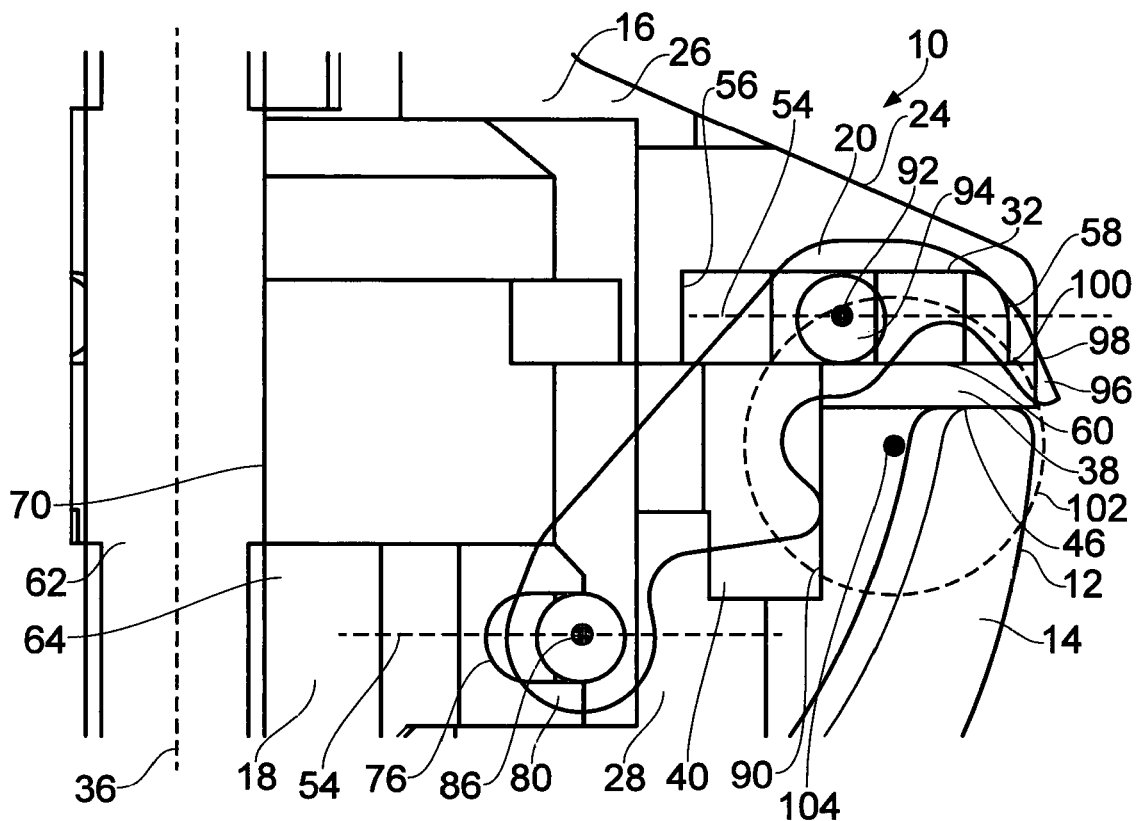
FIG. 2 is an axial cross-sectional view of the impactor head of FIG. 1, shown in an implant-release condition at the beginning of a gripping phase of a cup implant, which also corresponds to the end of a release phase of the cup implant.
Figure 3:
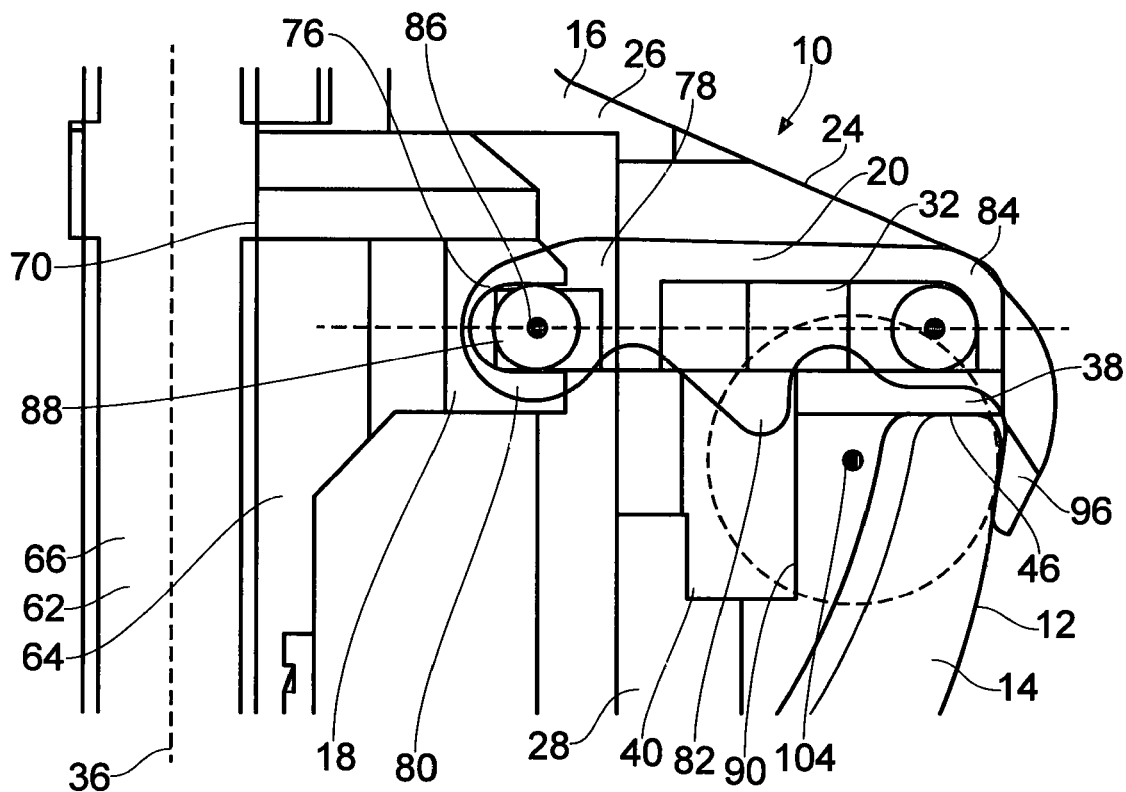
FIG. 3 is an axial cross-sectional view of the impactor head of FIG. 1, similar to that of FIG. 2 and shown in an implant-engagement condition gripping the cup implant.

Referring firstly to FIGS. 1 to 3, there is shown a first embodiment of an impactor head 10 for releasably holding an outer surface 12 of a cup implant 14. The impactor head 10 comprises a head body 16, an actuation mechanism 18, and at least one rotatable implant-engagement arm 20.

The head body 16, being in this case at least partly hemispherical, is a supporting structure which is shaped to be at least partly insertable into an acetabular cup implant 14. The head body 16 may beneficially be formed of plastics or metals, or a combination thereof.

In this embodiment, one or more dimples 22 are formed on an outer head surface 24 of the head body 16. However, these may be omitted dependent on necessity.

As shown in FIG. 1, the head body 16 has a top body portion 26 and a bottom body portion 28, which are held together by fastening means, such as at least one internal screw and/or snap-fit engagement, by way of examples.

The top body portion 26 has a receiving head portion 30, at least one radial guiding channel 32, and at least one, but preferably three, arm-recesses 34 through which the implant-engagement arms 20 protrude out from the head body 16. Although the radial guiding channel 32 is preferably in the top body portion 26, it may be in, overlap and/or shared with the bottom body portion. Additionally or alternatively, a plurality of implant-engagement arms may be accommodated in a single arm-recess.

The bottom body portion 28 is at least in part hemispherical, and thus has a distal pole and a central axis 36, an overhanging lip 38 and at least one axial guiding channel 40. The distal pole may also be referred to as the distal head end 42; and the opposite end of the head body 16 may be referred to as the proximal head end 44. The bottom body portion 28 is dimensioned to be receivable in a cup implant 14, and thus the overhanging lip 38 preferably provides a seat for abutment of a rim 46 of the cup implant 14. In this case, the entire rim 46 seats flushly on the shoulder defined by the overhanging lip 38. This is beneficial in providing stability for impaction of the cup implant 14 during surgery. However, it is feasible that there may gaps or spaces between the rim and the overhanging lip and/or the overhanging lip may be discontinuous along the circumference of the head body.

Alternatively, the bottom body portion need not necessarily be hemispherical. Instead, it may be cylindrical or any shape that is able to fit within the cup implant whilst providing sufficient space for the internal components, such as the actuation mechanism. Additionally or alternatively, it may be feasible to accommodate the actuation mechanism entirely within the top body portion, whereby the bottom body portion does not or has limited protrusion into the cavity defined by the part-spherical inner surface of the cup implant.

The receiving head portion 30 comprises a head element 48 and a neck portion 50 which extends from the head element 48 to meet the main body 52 of the top body portion 26. In this case, the receiving head portion 30 is unitarily formed as a one-piece with the main body 52. However, the head element, neck portion and main body may be separate parts which are connected together. Although the receiving head portion 30 is, in this embodiment, circular or substantially circular in a plane perpendicular to the central axis 36, it may be non-circular, such as being multi-faceted and/or polygonal.

As shown in FIG. 2 or 3, the radial guiding channel 32 is an internal cavity or chamber primarily located in the top body portion 26. The cavity or aperture is longitudinally elongate along at least a radial axis 54 or radial direction of the head body 16 and has a medial wall 56, a lateral wall 58, and a radial-floor wall 60 in this case provided by the bottom body portion 28.

The lateral wall 58 is, in this case partially rounded, but it could be envisaged that the lateral wall may be fully planar. There is preferably a said radial guiding channel 32 adjacent to one or both opposing longitudinal sides of each implant-engagement arm 20.

In this arrangement, each arm-recess 34 is open, whereby a slot is provided in the outer head surface 24 of the top body portion 26. However, in an alternative embodiment, each implant-engagement arm may extend from the head body within a projecting sleeve or cover. The arm-recesses 34 in this case are equiangularly spaced apart. However, in some situations, it is envisaged that a Y-shaped configuration may be beneficial. In this arrangement, two or more said arm-recesses and their associated implant-engagement arms would be positioned closer together relative to one or more further arm-recesses and associated implant-engagement arms on a generally opposing side of the head body.

The axial guiding channel 40 is a cavity or aperture within the bottom body portion 28, adjacent to an implant-engagement arm 20. The axial guiding channel 40 is longitudinally elongate to provide a depth along an axis parallel to the central axis 36. Although in this embodiment, a plurality of discrete or separate axial guiding channels 40 are associated with the implant-engagement arms 20, it may be feasible to provide a single axial guiding channel formed as a continuous or semi-continuous ring or trough. Similarly, a single radial guiding channel formed as a continuous or semi-continuous ring or trough could be envisaged.

Preferably, the radial and axial guiding channels 32, 40 are each longitudinally elongate along a respective axis, whereby the respective axes are perpendicular or substantially perpendicular to each other.

In an alternative arrangement, the axis of the axial guiding channel may be at a non-perpendicular angle relative to the axis of the radial guiding channel.

In a further alteration to the present embodiment, the axis of one of or both the axial and the radial guiding channels may be at least partly curved. Furthermore, the radial guiding channel may be partly curved and continuously transitions into the axial guiding channel without forming an edge.

The impactor head 10 has an actuation mechanism 18 which is, in this case, at least partly housed within the head body 16. The actuation mechanism 18 includes an actuator body 62 and an axially-translatable actuator 64.

The actuator body 62 is, in this arrangement, an elongate cylindrical core shaft 66 extending from the receiving head portion 30 towards the distal pole or distal head end 42 of the bottom body portion 28, such that the elongate core shaft 66 is coaxial with the central axis 36. Although preferably coaxial, it can be envisaged that the core shaft may be offset from the central axis.

The core shaft 66 is made of metal, plastics, or any combination thereof. The core shaft 66 may be a solid or tubular, and cylindrical or substantially cylindrical. The core shaft 66 has a top actuator surface 68, and an outer radial core surface 70. The core shaft 66 is threaded and preferably the thread is on the outer radial core surface 70.

Alternatively, the core shaft may have at least one elongate groove, slit or through-hole, within which a portion of the axially-translatable actuator may be receivable. Alternatively, there may be an elongate protrusion receivable within the axially-translatable actuator. The slit or elongate protrusion may be elongate at least in part in an axial direction. The slit may be linearly elongate in the axial direction only, such that the axially-translatable actuator may move linearly axially away from or in the direction of the proximal head end without the core shaft being rotatable. Alternatively, the slit or groove may be helical around the core shaft, such that rotation of the core shaft causes the axially-translatable actuator to be made to move linearly axially.

In an alternative embodiment, the core shaft may have another mechanism for moving the axially-translatable actuator, such as magnets, cranks or a cable or hydraulic transmission system, and/or electrically actuated via a servo motor or solenoid.

In this case, the top actuator surface 68 has a tool-receivable recess 72, shaped to receive a head of a rotation tool 74.

The axially-translatable actuator 64, which in this embodiment is fully located within the head body 16, comprises a shaft-facing surface having a portion of a thread complementarily engageable with the thread of the core shaft 66. In this way, the rotational motion of the core shaft 66 causes the axially-translatable actuator 64 to move linearly along the core shaft 66, with the direction depending on the direction of rotation of the top actuator surface 68.

The axially-translatable actuator 64 also includes an actuator recess 76, as shown in FIGS. 2 and 3. There may be one single axially-translatable actuator 64 entirely or substantially entirely surrounding the core shaft 66, having one actuator recess 76 for each implant-engagement arm 20 or a pair of adjacent implant-engagement arms 20. Alternatively, there may be multiple axially-translatable actuators per head body, each axially-translatable actuator having one or multiple actuator recesses, for operating implant-engagement arms separately.

The actuator recess 76 is slightly elongate radially relative to the central axis 36 to receive a part of an implant-engagement arm 20. In this way, during axial movement of the axially-translatable actuator 64, the implant-engagement arm 20 is able to move linearly radially within the actuator recess 76. In this case, the impactor head 10 has at least one, and preferably three, rotatable implant-engagement arms 20.

The or each implant-engagement arm 20 has an arm body 78 which is longitudinally elongate along a substantially radial axis 54 of the head body 16. The or each implant-engagement arm 20 may be moveable within a plane comprising the central axis 36 or alternatively, the plane may be offset from the central axis.

The arm body 78 has a medial arm end 80, a guiding protrusion 82 and a lateral arm end 84. The arm body 78 is rigid and may be made of plastics, metal or a combination thereof.

The medial arm end 80 is, in this case, rounded and has a medial pivot axis 86 formed by a medial pivot element 88, at or around which the medial arm end 80 is rotatable.

The medial pivot element 88 is translatable along an axis parallel to the central axis 36. Additionally, the medial pivot element 88 is translatable within the actuator recess 76, along an at least in part radial direction with respect to the central axis 36. In this case, the medial pivot element 88 is unable to translate relative to the arm body 78. Furthermore, the medial pivot element 88 is separate from the arm body 78, but in an alternative embodiment, the medial pivot element could be integrally formed with the arm body, for example, as one or more stub axles extending laterally from the arm body.

In an alternative embodiment, the medial pivot element may not be able to move linearly radially within the actuator recess, regardless of whether the medial pivot is separate or integrally formed with the arm body or whether the medial pivot is able or unable to translate relative to the arm body.

The guiding protrusion 82 is located between the medial arm end 80 and the lateral arm end 84 of the arm body 78 as shown in FIG. 2 or FIG. 3. The guiding protrusion 82 is preferably an integrally-formed rounded supporting portion, which extends at an angle to the longitudinal extent of the arm body 78. The guiding protrusion 82 may also have a lateral extent to be received in the axial guiding channel 40. The guiding protrusion 82 abuts a radially lateral axial wall 90 of the axial guiding channel 40 against which the guiding protrusion 82 or portion is able to slide or translate axially. As shown in FIGS. 2 and 3, the lateral arm end 84 has a lateral pivot axis 92 defined by a lateral pivot element 94, around which the lateral arm end 84 is rotatable, along with a lateral hook portion 96. The medial and lateral pivot elements 88, 94 are preferably axles, but may be captive ball-bearings or rollers.

In this case, the lateral pivot element 94 does not translate relative to the arm body 78. Furthermore, the lateral pivot element 94 is, in this case, separate from the arm body 78, but the lateral pivot element could be integrally formed with the arm body. The lateral pivot element 94 does not move axially parallel to the central axis but is translatable in an at least in part radial direction. This radial translation is due to the lateral pivot element 94 being contained within the radial guiding channel 32. The most lateral extent of the lateral pivot element 94 translating along the radial axis 54 is bounded by the lateral wall 58 of the radial guiding channel 32. Additionally, the lateral pivot element 94 is preferably biased into a position abutting against the lateral wall 58 of the radial guiding channel 32 by a spring.

In an alternative arrangement, the lateral pivot element may translate at least partially in an axial direction, parallel to the central axis. This may be possible if, for example, the radial guiding channel were to be partly curved and/or were to continuously transition into the axial guiding channel, without forming an edge. In a further alternative arrangement, the lateral pivot element may coincide with the guiding protrusion.

The spring has a first spring end and a second spring end. The first spring end is attached to the head body 16 whilst the second spring end is connected at or adjacent to the lateral pivot element 94. Preferably, in this case, the first spring end is attached to the medial wall 56, in which case the spring is a compression spring, for biasing the lateral pivot element 94 away from the central axis 36 in a radial direction.

In an alternative embodiment, the spring could be an extension spring having the first spring end attached to the lateral wall. In a further alternative to the current embodiment, a magnet may be contained within or placed upon the lateral pivot element and the complementary magnet of opposite polarity may be on or adjacent to the lateral wall. Alternatively or additionally, a magnet of polarity identical to that of the lateral pivot element may be placed in or on the medial wall of the radial guiding channel. Furthermore, in addition to the above arrangements, the medial pivot element may be biased into a certain position by a spring and/or a magnet.

In this case, the lateral hook portion 96 is integrally-formed with the arm body 78 and is preferably made of a biocompatible material, such as plastics or metal although other materials may be possible. The lateral hook portion 96 is finger-like to protrude in depending fashion from the top body portion 26. The lateral hook portion 96 has an outwards-facing surface 98 and an implant outer-surface engagement element 100 or cup-facing surface which contacts the outer surface 12 of a cup implant 14. The outwards-facing surface 98 in this case is curved, although it could alternatively be linear in cross-section.

Whilst in this case the lateral hook portion 96 is integrally formed with the arm body 78, in an alternative arrangement, the lateral hook portion may be hingeably connected to the arm and/or may be fully separable. The lateral hook portion may alternatively be at least partially retractable within the arm body, whether the lateral hook portion is linear or curved in cross-section.

The implant outer-surface engagement element 100 is preferably complementarily shaped to a prosthetic cup outer surface 12 and may be partly curved. To aid with gripping, the implant outer-surface engagement element may be coated with a gripping layer such as rubber or another suitable material. This may also reduce a risk of damage to the outer surface of a cup implant.

During translation and rotation into or out of the implant-engagement condition, the implant outer-surface engagement element 100 moves through a series of positions which describe a movement path 102, also referred to as an implant-engagement path, a release path or a virtual locus.

The movement of the lateral hook portion 96, starting with being out of the implant-engagement condition or in the implant-release condition and finishing upon being in the implant-engagement condition is referred to as the 'gripping phase' or 'cup-gripping phase'. The opposite movement, starting with being in the implant-engagement condition and finishing with being in the implant-release condition is the 'release phase.'

In this case, the axial cross-sectional geometry of the movement path 102 is an approximate arc of an ellipse or a circle around the rim 46 of a cup implant 14, the circle being centred around a, preferably dynamically-movable, virtual pivot point 104 as shown in FIGS. 2 and 3. The ellipse or circle may be changing in dimensions or be of fixed dimensions. In this case, both of these features may occur at different parts or sub-phases of the gripping and release phases.

Figure 4:
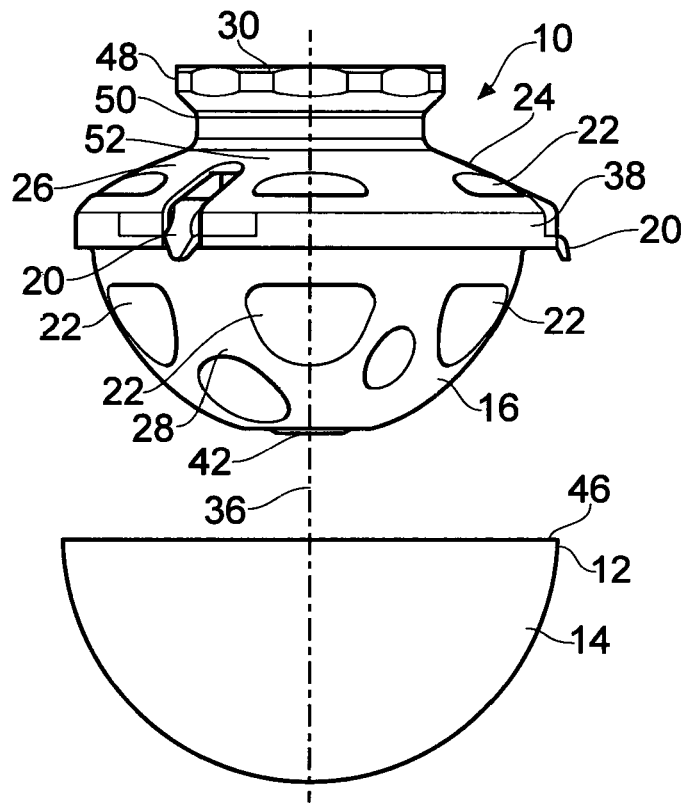
FIG. 4 shows the in-use impactor head aligned for engagement with a cup implant.
Figure 5:
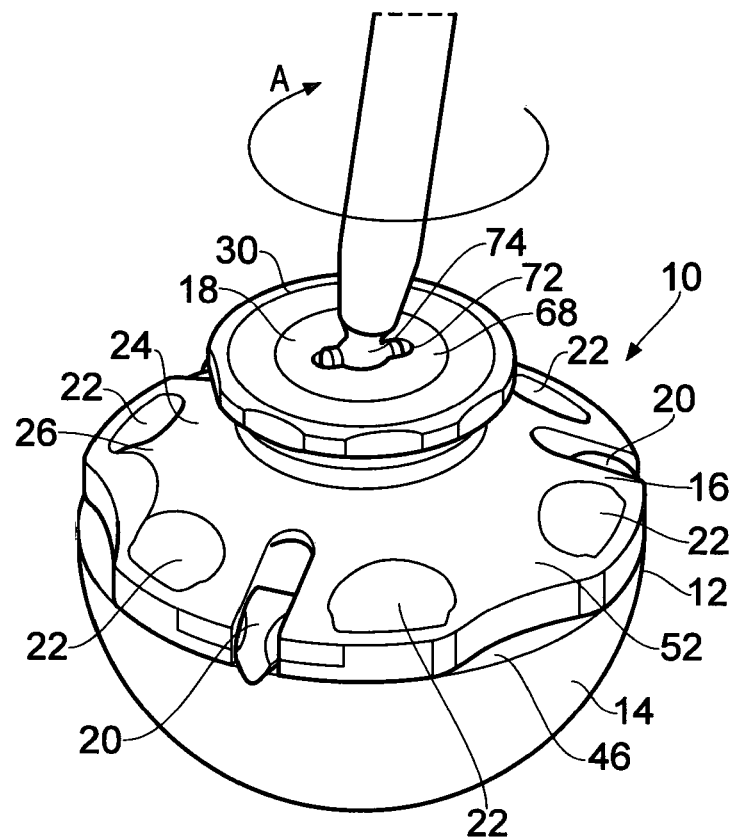
FIG. 5 is a perspective view from above showing the impactor head and cup implant engaged, and with the shaft of a rotation tool operating an actuation mechanism of the impactor head to grip the cup implant.
Figure 8:
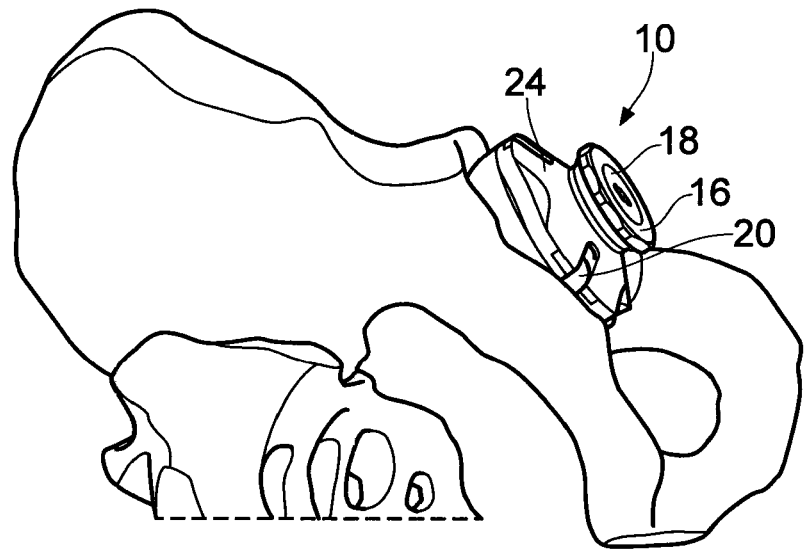
FIG. 8 is a view similar to FIG. 7, but showing the introducer released and removed from the impactor head.
Figure 6:
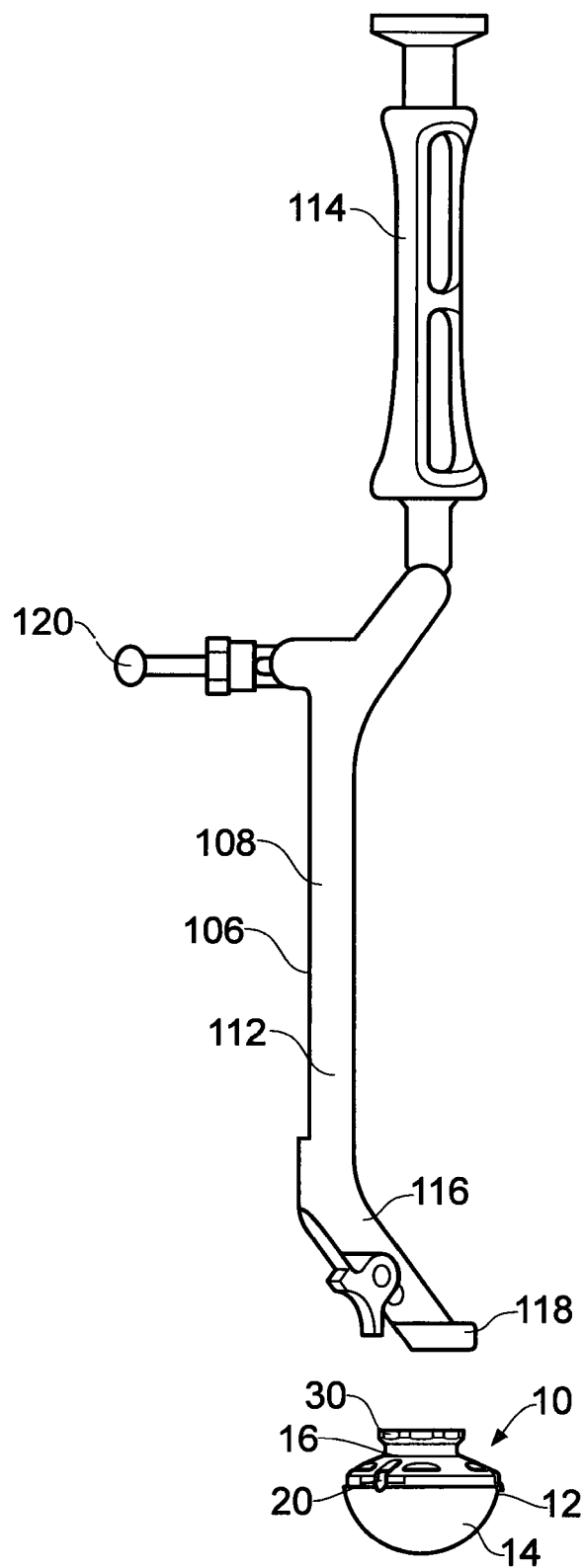
FIG. 6 shows one embodiment of a surgical introducing kit, in accordance with the third aspect of the invention, having an introducer in combination with the impactor head of FIG. 1, the impactor head being shown in its pre-engagement condition for clarity.

The virtual pivot point 104 is, in this case, separate and spaced below the lateral pivot element 94 in an axially proximal-to-distal direction of the impactor head 10 throughout at least part of the cup-release phase and at least a first part of the cup-gripping phase. In a second part of the cup-gripping phase, the virtual pivot point 104 may travel to coincide with the lateral pivot element 94. In use and with reference to FIGS. 1 to 9, to grasp an acetabular cup implant 14 with the impactor head 10, the user first inserts the bottom body portion 28 of the head body 16 into the cup implant 14, as shown in FIG. 4, such that the overhanging lip 38 abuts the rim 46 of the cup implant 14. The rotation tool 74, shown in FIG. 5, is engaged with the actuator recess 76 and operated to actuate the actuation mechanism 18. Rotary motion in one direction of the rotation tool 74, indicated as Arrow A, is imparted to the top actuator surface 68 integrally formed with the actuator body 62. The rotation may be clockwise or anti-clockwise depending on the orientation of the thread on the core shaft 66. Rotation of the actuator body 62 causes the axially-translatable actuator 64 to translate linearly along the central axis 36 in a direction of the proximal head end 44 of the impactor head 10. See FIG. 2.

The translation of the axially-translatable actuator 64 towards the proximal head end 44 causes the medial pivot element 88 to translate axially along the central axis 36, also in the direction of the proximal head end 44. The medial arm end 80 of the implant-engagement arm 20 pivots around the medial pivot element 88 and the lateral arm end 84 pivots around the lateral pivot element 94.

During a first part of the gripping phase, the radially translatable lateral pivot element 94 is biased away from the central axis 36 by the or multiple springs. The lateral translation in a radial direction may be, in this case, at least partly counteracted by the guiding protrusion 82 abutting the axial guiding channel 40, as shown in FIG. 2. In this case, the guiding protrusion 82 is axially-translatable whilst abutting the axial guiding channel 40. However, in an alternative arrangement, the guiding protrusion may be fixed and unable to translate axially.

In a further modification to the present embodiment, the guiding protrusion may be able to translate along a radial direction in addition to or instead of an axial direction.

In this case, during a second part of the gripping phase, the lateral pivot element 94 abuts the lateral wall 58 of the radial guiding channel 32, biased into position by the or multiple springs. Thus, during the second part of the gripping phase, the lateral pivot element 94 does not translate radially outwards.

When the pivoting implant-engagement arm 20 is moved from an implant-release condition into the implant-engagement condition by being rotated about both the medial and the lateral pivot elements 88, 94 and, during the first part of the gripping phase, translated laterally along a radial axis 54, the lateral hook portion 96 is moved out of the head body 16, along the movement path 102 around the cup rim 46.

The movement path 102 is arcuate about the virtual pivot point 104. In this case, during the first part of the gripping phase, the virtual pivot point 104 is inwards of the outer surface 12, and below the rim 46 of the cup implant 14. During the second part of the gripping phase, the virtual pivot point 104 coincides with the lateral pivot element 94. As such, the virtual pivot point 104 is above the rim 46 of the cup implant 14. In an alternative embodiment, at any time of the gripping phase or during the release phase the virtual pivot point may be above the rim and/or outwards of the cup and/or may be partly translatable or fixed. The virtual pivot point may coincide with the guiding protrusion or may be spaced-apart from the guiding protrusion.

The virtual pivot point 104 being dynamically-movable or dynamically-varying is due to having a plurality of pivot axes on a single body, the arm body 78. Due to the interactions of the translating medial and lateral pivot elements 88, 94, and the guiding protrusion 82 during the first part of the gripping phase, the movement path 102 can be described as approximately elliptical and/or an arc around a circle decreasing in diameter. The virtual pivot point 104 in this case may be considered to be translating radially outwards.

During the second part of the gripping phase, the movement path 102 is rotated about the virtual pivot point 104 which now coincides with the lateral pivot element 94. As such, the movement path 102 is an arc of a circle of unchanging diameter. The movement path 102 may transition smoothly between the two parts of the gripping phase, without forming an edge. This is the case if the longitudinal extent of arm body 78 is parallel or substantially parallel to a radius of the head body 16 at the transition between the first and second parts of the gripping phase.

In an alternative embodiment, the movement path at the transition between the first and second parts of the gripping phase may form an edge. This might be the case if the lateral hook portion is hinged or if the arm body is not aligned solely along a radial direction at the transition between the first and second parts of the gripping phase.

The implant outer-surface engagement element 100 engages with the outer surface 12 of the cup implant 14, thus enabling the impactor head 10 to grasp the cup implant 14 as shown in FIG. 3. The gripping force of the impactor head 10 can be increased by rotating the rotation tool 74 further. The head of the rotation tool 74 is then disengaged from the impactor head 10.

A surgical introducing kit or surgical introducing tool kit 106 comprising the impactor head 10 and a surgical introducer 108 is used to insert the prosthetic cup implant 14 into the hip 110. The surgical introducer 108 has an elongate impactor shaft 112 having a first end 114 shaped to be a graspable portion and a second end 116 having an attachment element 118. The attachment element 118 is preferably a releasably engageable clamp which is remotely operably by an operable lever 120. The releasably engageable clamp needs to be in the open position and arranged to receive the receiving head portion 30. See FIG. 6.

Figure 7:
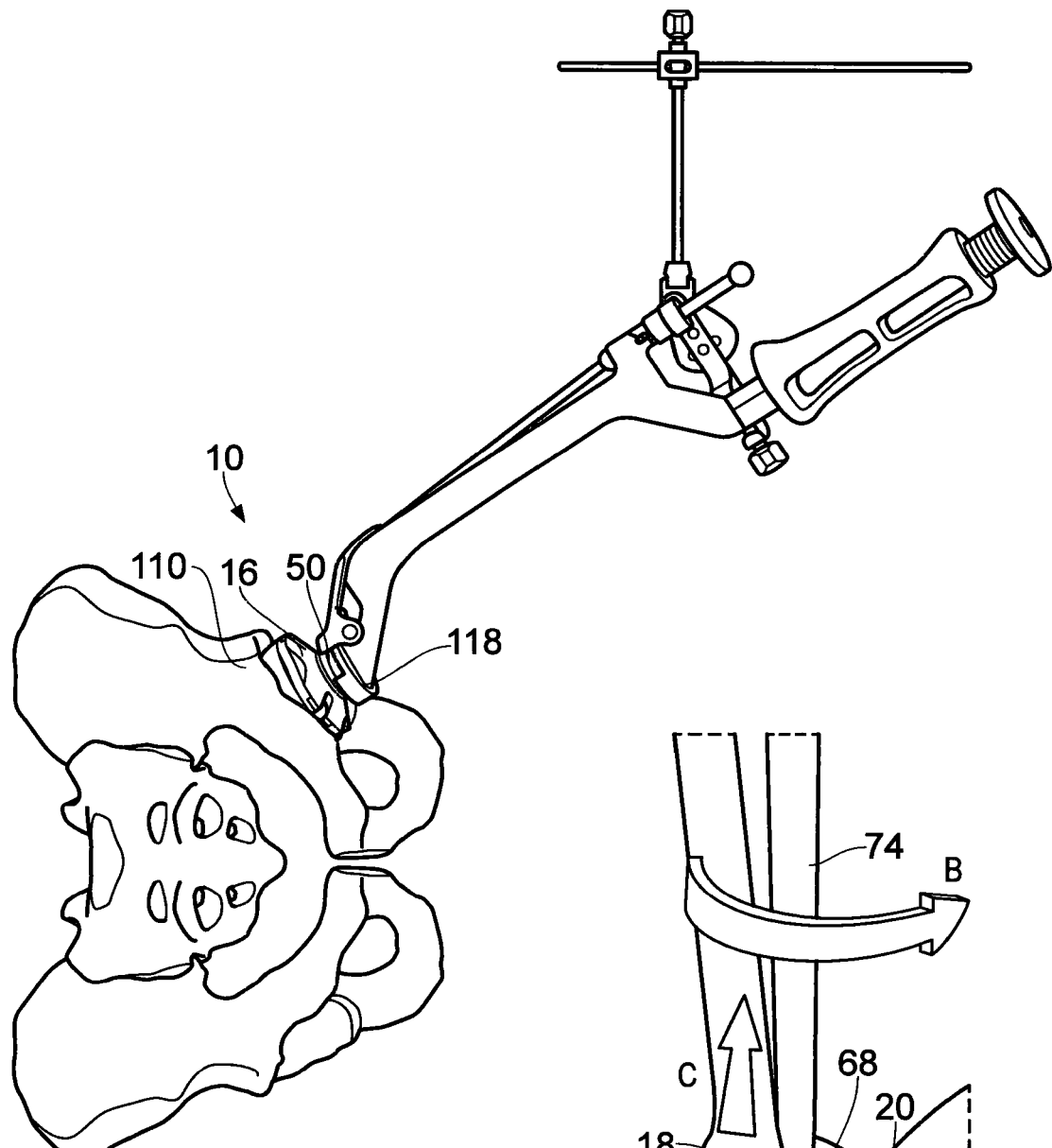
FIG. 7 shows the in-use surgical introducing kit positioning the cup implant into a patient's acetabulum.

The user than manipulates an operable lever 120, causing the clamping attachment element 118 to close around the receiving head portion 30 of the impactor head 10. The impactor head 10 holding the cup implant 14 is then inserted into a pre-drilled hole in the hip 110 as shown in FIG. 7 using the surgical introducer 108. The impactor shaft 112 may be used to verify the alignment of the impactor head 10, and thereby the cup implant 14 within the hip 110. Once the orientation of the cup implant 14 is correct, the operable lever 120 is operated to release the impactor head 10.

With the surgical introducer 108 removed, to disengage the impactor head 10 from the cup implant 14, the head of the rotation tool 74 is reengaged with the tool-receivable recess 72 of the top actuator surface 68. Rotary motion in the opposite direction to that of the gripping phase, indicated as Arrow B, is imparted to the top actuator surface 68, whilst the impactor head 10 is gripped by an anti-rotation tool. This motion causes the actuator body 62 to rotate in the opposite direction. Therefore, the axially-translatable actuator 64 and thus the medial pivot element 88 are made to translate linearly along the central axis 36 by the rotating actuator body 62 and towards the distal head end 42 of the impactor head 10.

When the rotatably translatable implant-engagement arm 20 is moved out of the implant-engagement condition by being rotated about at least the lateral pivot element 94 and preferably both the medial and lateral pivot elements 88, 94 and translated inwards along a radial direction, the lateral hook portion 96 is moved along the arcuate release path 102 and retracted into the head body 16 about the virtual pivot point 104. Upon travelling the arcuate release path 102, the lateral hook portion 96 does not move laterally beyond the movement path 102 followed during the gripping phase, resulting in a reduction of the bone removed or damaged.

Preferably, as the release phase is a mirror image of the gripping phase, the same movement path 102 is followed during the gripping and the release phases, in reverse order. As such, during the first part of the release phase when the virtual pivot point 104 and the lateral pivot element 94 coincide, the lateral hook portion 96 may move marginally laterally but in any event disengages by rotating around the lateral pivot element 94. During the second part of the release phase, the implant-engagement arm 20 additionally translates radially medially towards the central axis 36, resulting in the virtual pivot point 104 being spaced-apart from the lateral pivot element 94. Due to this inward translation, the lateral hook portion 96 does not travel laterally beyond its maximal lateral extent from the central axis 36 which occurs at the transition between the two parts of the release phase or the gripping phase.

Figure 9:
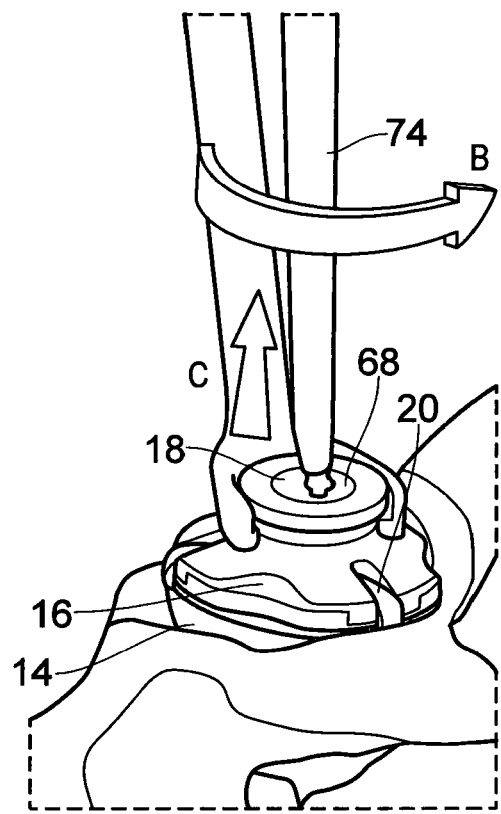
FIG. 9 shows the impactor head being gripped by an anti-rotation tool, and the rotation tool being used to release the impactor head from the cup implant.

The head of the rotation tool 74 is then disengaged from the impactor head 10 and the impactor head 10 is removed from the cup implant 14, indicated as Arrow C in FIG. 9. The impactor head 10 may be removed using an anti-rotation tool, a lifting tool or the surgical introducer 108.

In a modification to the above-described impactor head, the implant-engagement arm has at least one internal slot or channel in the arm body. The or each internal channel may be elongate along the same extent as the arm body. The or each internal channel is suitable for one of or a plurality of pivot elements to translate within the internal channel such that the or both pivot elements are translatable relative to the arm body. The pivot element or elements may be fixed relative to the head body or alternatively, may be translatable relative to both the head body and the arm body.

Figure 10:
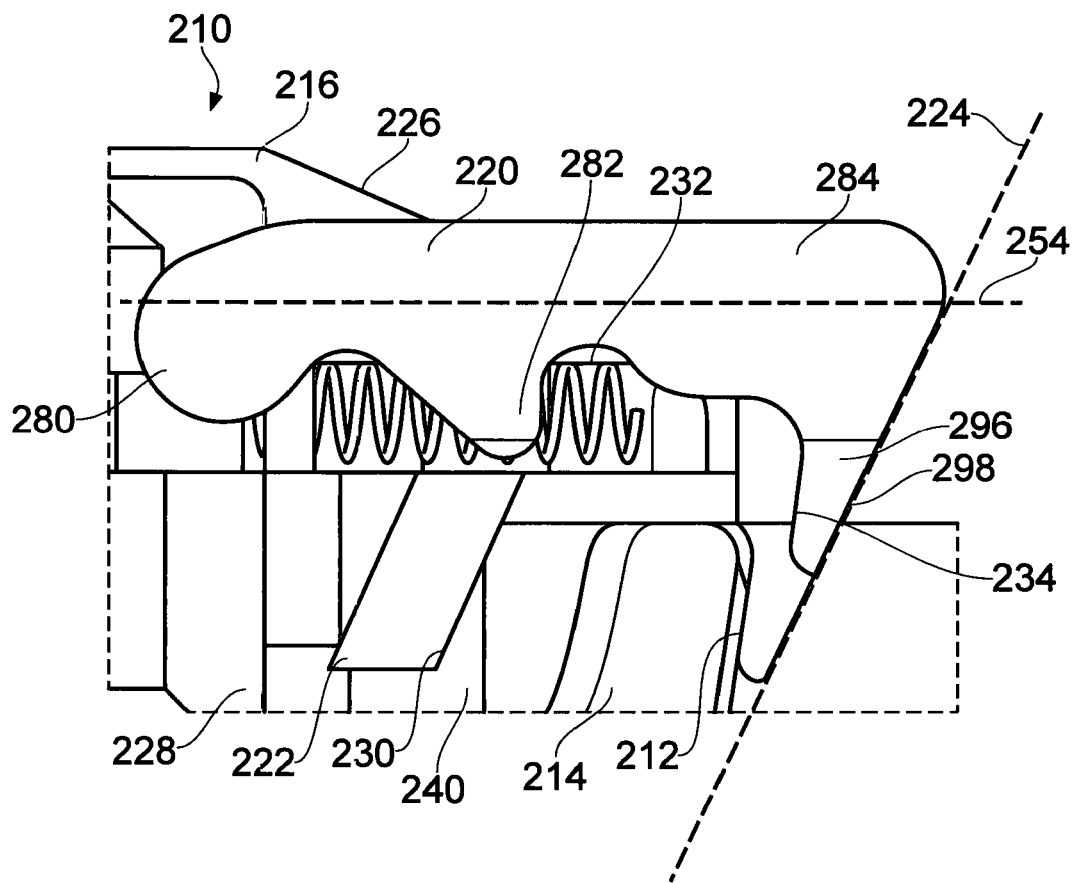
FIG. 10 shows a second embodiment of an impactor head, in accordance with the second aspect of the invention.

Now referring to FIG. 10, there is shown a second embodiment of an impactor head 210 for releasably holding an outer surface 212 of a cup implant 214. Features which are similar or identical to those of the first embodiment may use similar or identical references to those of the first embodiment, typically starting above '200'.

The head body 216 of the second embodiment is similar to the head body 16 of the first embodiment, having a top body portion 226, a bottom body portion 228, a radial guiding channel 232 and an actuation mechanism. Detailed description of the common features has been omitted for brevity. In this case, the head body 216 has a diagonal guiding channel 222 in addition to or instead of the axial guiding channel 40 of the first embodiment. The longitudinal extent of the diagonal guiding channel 222 is angled towards the distal pole or distal head end and is at an angle relative to the central axis.

The implant-engagement arm 220 of the second embodiment is similar to the implant-engagement arm 20 of the first embodiment, having a medial arm end 280, a lateral arm end 284, a lateral hook portion 296 and a guiding protrusion 282. Detailed description of common features is therefore again omitted for brevity.

In this case, the implant-engagement arm 220 is not rotatable. The arm in this embodiment is solely translatable simultaneously along a radial axis 254 and along an axial direction, such that the resulting direction of motion is a diagonal axis 224, along the axis defined by the diagonal guiding channel 222.

The implant-engagement arm 220 may still be biased away from the central axis, by a spring and/or another means such as a magnet. In this way, the guiding protrusion 282 is biased to run on the radially outer surface 230 of the diagonal guiding channel 222, similarly to the first embodiment. The lateral hook portion 296, in this case, has an outwards-facing surface 298 and cup-facing surface or an implant outer-surface engagement element 234 which opposes the outwards-facing surface 298. The outwards-facing surface 298 and the implant-outer surface engagement element 234 are arranged to taper towards each other in a direction of the distal head end.

An axial cross-sectional geometry of the movement path or virtual locus of the implant outer-surface engagement element 234 is linear. There is no virtual pivot point in this embodiment.

The uses of the second embodiment are similar to those of the first embodiment, using the surgical introducing kit and detailed description of the common features is here omitted for brevity.

Using the impactor head 210 of the second embodiment, during the gripping phase, the axially-translatable actuator causes the implant-engagement arm 220 to translate axially in the direction of the distal head end, instead of towards the proximal head end, along the core shaft. The diagonal guiding channel 222 forces the implant-engagement arm 220 to translate inwards along a radial direction, whilst the spring biases the implant-engagement arm 220 to move outwards, laterally along the radial direction relative to the central axis such that the guiding protrusion 282 abuts the radially outer surface 230. The path or virtual locus is a straight line, angled towards the distal pole, parallel with the longitudinal axis of the diagonal guiding channel 222. Thus, the head body 216 has a distal head end and the implant outer-surface engagement element 234 is moveable on a linear implant-engagement path angled towards the said distal head end of the head body 216 when moving towards the implant-engagement condition.

The implantation procedure of the cup implant 214 is similar to the procedure described in the first embodiment. During the release phase, the axially-translatable actuator is operated to translate along the core shaft in direction of the proximal head end, with the spring biasing the implant-engagement arm 220 laterally.

It is therefore possible to provide an impactor head for releasably holding an outer surface of a cup implant which, by having a gripping arm that both rotates along with translating inwardly and outwardly, minimises an amount of bone resection required to release the cup following insertion into a patient's acetabulum. Furthermore, it is also possible to provide an impactor head for releasably holding an outer surface of a cup implant, by having at least one non-rotatable implant-engagement arm which is translatable in both radial and axial directions. Such an impactor head also reduces the amount of bone resection required to release the cup implant. Additionally it is also possible to provide a surgical introducing kit and a method using either one of the said impactor heads for introducing the cup implant into an acetabulum during surgery whilst minimising the amount of bone resection needed during the cup implant release.

The words 'comprises/comprising' and the words 'having/including' when used herein with reference to the present invention are used to specify the presence of stated features, integers, steps or components, but do not preclude the presence or addition of one or more other features, integers, steps, components or groups thereof. It is appreciated that certain features of the invention, which are, for clarity, described in the context of separate embodiments, may also be provided in combination in a single embodiment. Conversely, various features of the invention which are, for brevity, described in the context of a single embodiment, may also be provided separately or in any suitable sub-combination. The embodiments described above are provided by way of examples only, and various other modifications will be apparent to persons skilled in the field without departing from the scope of the invention as defined herein.

The invention claimed is:

1. An impactor head for releasably holding an outer surface of a cup implant, the impactor head comprising a head body; at least one rotatable implant-engagement arm being at least in part translatable; an actuation mechanism which moves the implant-engagement arm to an implant-engagement condition or an implant-release condition; and an implant outer-surface engagement element which is at or adjacent to a lateral arm end of said implant-engagement arm, said implant-engagement arm including a lateral pivot axis about which the implant-engagement arm is rotatable to adopt said implant-engagement condition or said implant-release condition, the lateral pivot axis being radially translatable to move the implant-engagement arm radially as the implant-engagement arm rotates.

2. An impactor head as claimed in claim 1, wherein said implant-engagement arm has a lateral hook portion, the implant outer-surface engagement element being on an inner face of the lateral hook portion.

3. An impactor head as claimed in claim 1, wherein the head body includes a radial guiding channel in which the lateral pivot axis is slidable, so that the implant-engagement arm is translatable to linearly move radially as the implant-engagement arm rotates.

4. An impactor head as claimed in claim 1, wherein the said implant-engagement arm is translatably rotatable about a virtual pivot point, so that the implant outer-surface engagement element is able to follow an arcuate movement path about a rim of the cup implant.

5. An impactor head as claimed in claim 4, wherein the virtual pivot point is dynamically-movable.

6. An impactor head as claimed in claim 4, wherein the head body has a distal head end and wherein the virtual pivot point is spaced from the lateral pivot axis in a direction of the said distal head end during at least part of the translatable rotation of the said implant-engagement arm.

7. An impactor head as claimed in claim 1, wherein said implant-engagement arm includes a medial pivot axis about which the implant-engagement arm is rotatable to adopt said implant-engagement condition or said implant-release condition.

8. An impactor head as claimed in claim 7, wherein said actuation mechanism engages said medial pivot axis to operate the said implant-engagement arm.

9. An impactor head as claimed in claim 7, wherein the medial pivot axis is translatable to enable linear movement of the implant-engagement arm radially as it rotates.

10. An impactor head as claimed in claim 7, wherein the implant-engagement arm includes a further channel in which the medial pivot axis is slidable, so that the implant-engagement arm is translatable to linearly move radially as the implant-engagement arm rotates.

11. An impactor head as claimed in claim 1, wherein the actuation mechanism includes an actuator body receivable at least in part in the cup implant, and an axially-translatable actuator.

12. A method of reducing acetabulum bone damage during insertion of a cup implant gripped on its outer surface, the method comprising the steps of: (a) providing an implant-engagement arm of an impactor head, wherein the implant-engagement arm is rotatably translatable such that the implant-engagement arm has a dynamically-movable virtual pivot point; and (b) providing a release path on which an implant outer-surface engagement element travels, the release path originating at an implant-engagement condition of the implant outer-surface engagement element, so that, when moving to an implant-release condition, a bone space required to accommodate a lateral arm end of the implant-engagement arm is reduced, wherein the dynamically-movable virtual pivot point results in the implant outer-surface engagement element having at least a reduced movement outwardly when moving to the implant-release condition.

* * * * *